(12) United States Patent
Henkelmann et al.

(10) Patent No.: US 8,895,791 B2
(45) Date of Patent: Nov. 25, 2014

(54) METHOD OF REGENERATING RUTHENIUM CATALYSTS SUITABLE FOR HYDROGENATION

(75) Inventors: Jochem Henkelmann, Mannheim (DE); Michael Becker, Offenburg (DE); Daniela Mirk, Mannheim (DE); Felix Richter, Ludwigshafen (DE); Thomas Schäfer, Mannheim (DE)

(73) Assignee: BASF SE (DE)

( * ) Notice: Subject to any disclaimer, the term of this patent is extended or adjusted under 35 U.S.C. 154(b) by 977 days.

(21) Appl. No.: 12/375,566

(22) PCT Filed: Jul. 18, 2007

(86) PCT No.: PCT/EP2007/057428
§ 371 (c)(1),
(2), (4) Date: Jan. 29, 2009

(87) PCT Pub. No.: WO2008/015103
PCT Pub. Date: Feb. 7, 2008

(65) Prior Publication Data
US 2009/0281348 A1    Nov. 12, 2009

(30) Foreign Application Priority Data

Jul. 31, 2006  (EP) ..................................... 06118206

(51) Int. Cl.
| | | |
|---|---|---|
| *C07C 5/10* | (2006.01) | |
| *B01J 23/46* | (2006.01) | |
| *C07C 67/303* | (2006.01) | |
| *B01J 38/04* | (2006.01) | |
| *B01J 35/10* | (2006.01) | |
| *B01J 35/00* | (2006.01) | |
| *B01J 35/08* | (2006.01) | |
| *B01J 21/04* | (2006.01) | |
| *B01J 37/18* | (2006.01) | |

(52) U.S. Cl.
CPC ................ *C07C 5/10* (2013.01); *B01J 35/1038* (2013.01); *B01J 35/108* (2013.01); *B01J 35/1019* (2013.01); *C07C 2101/14* (2013.01); *B01J 35/0053* (2013.01); *B01J 35/08* (2013.01); *B01J 35/1061* (2013.01); *B01J 38/04* (2013.01); *B01J 21/04* (2013.01); *B01J 23/462* (2013.01); *B01J 35/008* (2013.01); *B01J 37/18* (2013.01); *C07C 67/303* (2013.01); *C07C 2523/46* (2013.01); *Y10S 585/906* (2013.01)
USPC ........... 585/277; 585/250; 585/266; 585/269; 585/275; 585/906; 502/34

(58) Field of Classification Search
USPC ......... 585/250, 266, 269, 275, 277, 904, 906; 502/514, 34
See application file for complete search history.

(56) References Cited

U.S. PATENT DOCUMENTS

| | | | |
|---|---|---|---|
| 2,757,128 A | 7/1956 | Hemminger | |
| 2,898,387 A | 8/1959 | Teter | |
| 3,591,522 A * | 7/1971 | Cosyns et al. | 502/31 |
| 3,597,489 A | 8/1971 | Vu et al. | |
| 3,851,004 A | 11/1974 | Yang | |
| 4,322,315 A * | 3/1982 | Drake | 502/30 |
| 4,331,557 A * | 5/1982 | Drake | 502/53 |
| 5,817,589 A * | 10/1998 | de Agudelo et al. | 502/53 |
| 6,077,983 A * | 6/2000 | Ono et al. | 585/269 |
| 6,388,149 B2 * | 5/2002 | Ruhl et al. | 585/254 |
| 7,355,084 B2 | 4/2008 | Böttcher et al. | |
| 7,388,119 B2 | 6/2008 | Böttcher et al. | |
| 2007/0060774 A1 * | 3/2007 | Okamoto et al. | 564/385 |
| 2007/0112210 A1 * | 5/2007 | Arndt et al. | 549/555 |

FOREIGN PATENT DOCUMENTS

| | | | | |
|---|---|---|---|---|
| CA | 2612435 | 12/2006 | | |
| DE | 19634880 | 10/1997 | | |
| DE | 19624485 | 1/1998 | | |
| DE | 10128242 | 12/2002 | | |
| DE | 10216745 | 10/2003 | | |
| DE | 102005029200 | 12/2006 | | |
| EP | 814098 | 12/1997 | | |
| EP | 0913194 | 5/1999 | | |
| EP | 1169285 | 1/2002 | | |
| GB | 799396 | 8/1958 | | |
| JP | 01159059 | 6/1989 | | |
| JP | 3068453 | 3/1991 | | |
| JP | 2000051701 | 2/2000 | | |
| WO | WO-0063142 | 10/2000 | | |
| WO | WO-03010119 | 2/2003 | | |
| WO | WO 2005061106 A1 * | 7/2005 | | B01J 23/46 |

OTHER PUBLICATIONS

English-language translation of the International Preliminary Report on Patentability issued in international application PCT/EP2007/057428, mailed Mar. 19, 2009.

* cited by examiner

*Primary Examiner* — In Suk Bullock
*Assistant Examiner* — Bradley Etherton
(74) *Attorney, Agent, or Firm* — Drinker Biddle & Reath LLP

(57) ABSTRACT

The present invention relates to a method of regenerating a ruthenium catalyst suitable for hydrogenation, which comprises flushing the catalyst with inert gas in a regeneration step until the original activity or part of the original activity has been attained. The method is particularly useful for ruthenium catalysts which are used for the hydrogenation of aromatics.

14 Claims, No Drawings ural effects on the catalyst, for example by blocking of the catalytically active sites or by loss of catalytically active sites as a result of thermal, mechanical or chemical processes. For example, catalyst deactivation or

METHOD OF REGENERATING RUTHENIUM CATALYSTS SUITABLE FOR HYDROGENATION

CROSS REFERENCE TO RELATED APPLICATIONS

This application is a National Stage of PCT/EP2007/057428 filed Jul. 18, 2007 which in turn claims priority from European Application 06118206.9 filed Jul. 31, 2006, the entire contents of which are incorporated herein by reference.

The present invention relates to a method of regenerating a ruthenium catalyst which is, in particular, suitable for the hydrogenation of optionally substituted monocyclic or polycyclic aromatics to the corresponding cycloaliphatics.

There are numerous processes for the hydrogenation of aromatics, for instance of benzene to cyclohexane. These hydrogenations are predominantly carried out over nickel and platinum catalysts in the gas phase or liquid phase. Such hydrogenation processes are disclosed, inter alia, in U.S. Pat. No. 3,597,489, U.S. Pat. No. 2,898,387 or GB 799 396. Typically, the major part of the benzene is firstly hydrogenated to cyclohexane in a main reactor and the conversion into cyclohexane is subsequently completed in one or more after-reactors.

A particularly useful catalyst which can be used in the hydrogenation of aromatic compounds is disclosed in DE 196 24 485 A1. The catalyst comprises, as active metal, either ruthenium alone or ruthenium together with at least one metal of transition group I, VII or VIII of the Periodic Table (CAS version) in an amount of from 0.01 to 30% by weight, based on the total weight of the catalyst, and is applied to a support. From 10 to 50% of the pore volume of the support is formed by macropores having a pore diameter in the range from 50 nm to 10000 nm and from 50 to 90% of the pore volume of the support is formed by mesopores having a pore diameter in the range from 2 to 50 nm, with the sum of the pore volumes being 100%. Supports used are activated carbon, silicon carbide, aluminum oxide, silicon dioxide, titanium dioxide, zirconium dioxide, magnesium dioxide, zinc oxide or a mixture of two or more thereof.

Further particularly useful catalysts for the hydrogenation of aromatic compounds are disclosed in EP-A 1 169 285. In one embodiment (catalyst 1), the catalyst comprises at least one metal of transition group VIII of the Periodic Table (CAS version) applied to a support, with the support having macropores and the catalyst comprising, as active metal, at least one metal of transition group VIII of the Periodic Table, either alone or together with at least one metal of transition group I or VII of the Periodic Table, applied to a support, with the support having a mean pore diameter of at least 50 nm and a BET surface area of not more than 30 m²/g and the amount of active metal being from 0.01 to 30% by weight, based on the total weight of the catalyst. In a further embodiment (catalyst 2), the catalyst comprises, as active metal, at least one metal of transition group VIII of the Periodic Table, either alone or together with at least one metal of transition group I or VII of the Periodic Table in an amount of from 0.01 to 30% by weight, based on the total weight of the catalyst, applied to a support, with from 10 to 50% of the pore volume of the support being formed by macropores having a pore diameter in the range from 50 nm to 10000 nm and from 50 to 90% of the pore volume of the support being formed by mesopores having a pore diameter in the range from 50 nm to 10000 nm and from 50 to 90% of the pore volume of the support being formed by mesopores having a pore diameter in the range from 2 to 50 nm, with the sum of the proportions of the pore volumes being 100%. Supports used are activated carbon, silicon carbide, aluminum oxide, silicon dioxide, titanium dioxide, zirconium dioxide, magnesium dioxide, zinc oxide or a mixture of two or more thereof, preferably aluminum oxide.

Finally, a further particularly useful catalyst is disclosed in the patent application DE 102 005 029 200. This is a coated catalyst comprising, as active metal, either ruthenium alone or ruthenium together with at least one further metal of transition group IB, VIIB or VIII of the Periodic Table of the Elements (CAS version) applied to a support comprising silicon dioxide as support material, wherein the amount of active metal is <1% by weight, based on the total weight of the catalyst, and at least 60% by weight of the active metal is present in the shell of the catalyst to a penetration depth of 200 µm, determined by means of SEM-EPMA (EXDS).

The maintenance of the catalyst activity over a very long period of time is of great economic importance for industrial processes.

A decrease in the catalytic activity is usually caused by various physical and chemical effects on the catalyst, for example by blocking of the catalytically active sites or by loss of catalytically active sites as a result of thermal, mechanical or chemical processes. For example, catalyst deactivation or aging in general can be caused by sintering of the catalytically active sites, by loss of (noble) metal, as a result of deposits or by poisoning of the active sites. There are many aging/deactivation mechanisms.

Conventionally, the deactivated catalyst has to be removed from the reactor for regeneration. The reactor is then down, or abrasion is resumed after installation of another catalyst or switching over to a previously installed further catalyst. In either case, this leads to significant costs. The U.S. Pat. Nos. 3,851,004 and 2,757,128 disclose processes for the hydrogenation of, inter alia, olefins in hydrocarbon starting materials and the regeneration of the catalysts by means of hydrogen.

DE 196 34 880 C2 discloses a process for the simultaneous selective hydrogenation of diolefins and nitriles from a hydrocarbon starting material. In this process, the catalyst is, after its diolefin hydrogenation activity has dropped to less than 50% of the initial activity, flushed with an inert gas to remove traces of the hydrocarbon from the catalyst and to produce a flushed catalyst and this is flushed with hydrogen in a subsequent regeneration step. This produces a regenerated catalyst whose diolefin hydrogenation activity is once again at least 80% of the initial value.

Deactivation is likewise observed in the hydrogenation of aromatics using the ruthenium catalysts described, and this deactivation has not yet been able to be overcome in a simple way.

It is an object of the present invention to provide a method of regenerating a ruthenium catalyst used in hydrogenations. This should be simple to implement in terms of apparatus and be inexpensive to carry out. In particular, multiple and complete regeneration of the catalyst is said to be able to be achieved thereby.

The above object is achieved by a method of regenerating a ruthenium catalyst for the hydrogenation of aromatics, which comprises flushing the catalyst with inert gas in a regeneration step until the original activity or part of the original activity has been attained.

This regeneration firstly results in higher conversions due to an increased catalyst activity, and, secondly, the catalyst operating lives in production operation are significantly increased by means of the method of the invention.

The method of the invention is particularly suitable for regeneration of Ru catalysts which are described in the patent applications EP-A 0 814 098, EP-A 1 169 285 and DE 102 005 029 200 are used in the processes disclosed there. These catalysts and processes are described below.

In all of the present patent application, the groups of the Periodic Table are designated according to the CAS version.

Preferred Catalysts

EP-A 0 814 098

The catalysts described below are designated as "catalyst variant I" in the present patent application.

As active metals, it is in principle possible to use all metals of transition group VIII of the Periodic Table. Preference is given to using platinum, rhodium, palladium, cobalt, nickel or ruthenium or a mixture of two or more thereof as active metals, with particular preference being given to using ruthenium as active metal.

The terms "macropores" and "mesopores" are, for the purposes of the present invention, used in accordance with the definition in *Pure Appl. Chem.*, 45, p. 79 (1976), namely pores whose diameter is above 50 nm (macropores) or whose diameter is in the range from 2 nm to 50 nm (mesopores). "Micropores" are likewise defined in the references cited above and denote pores having a diameter of <2 nm.

The active metal content is generally from about 0.01 to about 30% by weight, preferably from about 0.01 to about 5% by weight and in particular from about 0.1 to about 5% by weight, in each case based on the total weight of the catalyst used.

The total metal surface area in catalyst variant I is preferably from about 0.01 to about 10 $m^2/g$, more preferably from about 0.05 to about 5 $m^2/g$ and in particular from about 0.05 to about 3 $m^2/g$, of the catalyst. The metal surface area is determined by means of the chemisorption method described by J. Lemaitre et al. in "*Characterization of Heterogeneous Catalysts*", Editor: Francis Delanney, Marcel Dekker, New York 1984, pp. 310-324.

In catalyst variant I, the ratio of the surface areas of the active metal/metals and the catalyst support is preferably less than about 0.05, with the lower limit being about 0.0005.

Catalyst variant I comprises a support material which is macroporous and has a mean pore diameter of at least about 50 nm, preferably at least about 100 nm, in particular at least about 500 nm, and whose BET surface area is not more than about 30 $m^2/g$, preferably not more than about 15 $m^2/g$, more preferably not more than about 10 $m^2/g$, in particular not more than about 5 $m^2/g$ and more preferably not more than about 3 $m^2/g$. The mean pore diameter of the support is preferably from about 100 nm to about 200 μm, more preferably from about 500 nm to about 50 μm. The BET surface area of the support is preferably from about 0.2 to about 15 $m^2/g$, more preferably from about 0.5 to about 10 $m^2/g$, in particular from about 0.5 to about 5 $m^2/g$ and more preferably from about 0.5 to about 3 $m^2/g$.

The surface area of the support is determined by the BET method by means of $N_2$ adsorption, in particular in accordance with DIN 66131. The determination of the mean pore diameter and the pore size distribution is carried out by means of Hg porosimetry, in particular in accordance with DIN 66133.

The pore size distribution of the support can preferably be approximately bimodal, with the pore diameter distribution having maxima at about 600 nm and about 20 μm in the bimodal distribution representing a specific embodiment of the invention.

Further preference is given to a support which has a surface area of 1.75 $m^2/g$ and has this bimodal distribution of the pore diameter. The pore volume of this preferred support is preferably about 0.53 ml/g.

As macroporous support material, it is possible to use, for example, macropore-comprising activated carbon, silicon carbide, aluminum oxide, silicon dioxide, titanium dioxide, zirconium dioxide, magnesium oxide, zinc oxide or mixtures of two or more thereof, with preference being given to using aluminum oxide and zirconium dioxide.

Corresponding catalyst supports and methods of producing them are disclosed in the following documents:

Fundamentals of Industrial Catalytic Processes, R. J. Farrauto, C. H. Bartholomew, First Edition 1997, pages 16, 17, 57 to 62, 88 to 91, 110 to 111; Oberlander, R. K., 1984 Aluminas for Catalysts, in Applied Industrial Catalysis, e.g. D. E. Leach, Academic Press, Vol. 3, Chapter 4; U.S. Pat. No. 3,245,919; WO 93104774; EP-A 0 243 894; Ullmann's Encyclopedia of Industrial Chemistry, 5. Ed., Vol. Al, p. 588 to 590; VCH 1985.

EP-A 1 169 285

The catalysts described below are designated as "catalyst variant II" in the present patent application. There are various subvariants of this variant II.

Subvariant 1

This catalyst corresponds to those described above under EP-A 0 814 089.

A description is also given in EP-A 1 169 285 of the subvariant 1a used according to the invention, which represents a preferred embodiment of subvariant 1. Support materials which can be used are ones which are macroporous and have a mean pore diameter of at least 0.1 μm, preferably at least 0.5 μm, and a surface area of not more than 15 $m^2/g$, preferably not more than 10 $m^2/g$, particularly preferably not more than 5 $m^2/g$, in particular not more than 3 $m^2/g$. The mean pore diameter of the support used there is preferably in the range from 0.1 to 200 μm, in particular from 0.5 to 50 μm. The surface area of the support is preferably from 0.2 to 15 $m^2/g$, particularly preferably from 0.5 to 10 $m^2/g$, in particular from 0.5 to 5 $m^2/g$, especially from 0.5 to 3 $m^2/g$, of the support. This catalyst, too, has the above-described bimodality of the pore diameter distribution with the analogous distributions and the correspondingly preferred pore volume. Further details regarding subvariant 1a may be found in DE-A 196 04 791.9 whose contents are fully incorporated by reference into the present patent application.

Subvariant 2

Subvariant 2 comprises one or more metals of transition group VIII of the Periodic Table as active component(s) on a support as defined herein. Ruthenium is preferably used as active component.

The total metal surface area on the catalyst is preferably from 0.01 to 10 $m^2/g$, particularly preferably from 0.05 to 5 $m^2/g$ and more preferably from 0.05 to 3 $m^2/g$, of the catalyst. The metal surface area was measured by the chemisorption method described in J. Lemaitre et al., "*Characterization of Heterogeneous Catalysts*", Editor: Francis Delanney, Marcel Dekker, New York (1984), pp. 310-324.

In subvariant 2, the ratio of the surface areas of the at least one active metal and the catalyst support is less than about 0.3, preferably less than about 0.1 and in particular about 0.05 or less, with the lower limit being about 0.0005.

The support materials which can be used in subvariant 2 have macropores and mesopores.

The supports which can be used have a pore distribution in which from about 5 to about 50%, preferably from about 10 to about 45%, more preferably from about 10 to about 30% and in particular from about 15 to about 25%, of the pore volume is formed by macropores having pore diameters in the range from about 50 nm to about 10000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm, with the sum of the proportions of the pore volumes in each case being 100%.

The total pore volume of the support used is from about 0.05 to 1.5 $cm^3/g$, preferably from 0.1 to 1.2 $cm^3/g$ and in particular from about 0.3 to 1.0 $cm^3/g$. The mean pore diameter of the supports used according to the invention is from about 5 to 20 nm, preferably from about 8 to about 15 nm and in particular from about 9 to about 12 nm.

The surface area of the support is preferably from about 50 to about 500 $m^2/g$, more preferably from about 200 to about 350 $m^2/g$ and in particular from about 250 to about 300 $m^2/g$, of the support.

The surface area of the support is determined by the BET method by means of $N_2$ adsorption, in particular in accordance with DIN 66131. The determination of the mean pore diameter and the size distribution is carried out by means of Hg porosimetry, in particular in accordance with DIN 66133.

Although it is in principle possible to use all support materials known in catalyst production, i.e. those which have the above-defined pore size distribution, preference is given to using activated carbon, silicon carbide, aluminum oxide, silicon dioxide, titanium dioxide, zirconium dioxide, magnesium oxide, zinc oxide and mixtures thereof, more preferably aluminum oxide and zirconium dioxide.

DE 102 005 029 200

The catalysts disclosed below are designated as catalyst variant III or "coated catalysts" in the present patent application.

The subject matter is a coated catalyst comprising, as active metal, either ruthenium alone or ruthenium together with at least one further metal of transition group IB, VIIB or VIII of the Periodic Table of the Elements (CAS version) applied to a support comprising silicon dioxide as support material.

In this coated catalyst, the amount of active metal is <1% by weight, preferably from 0.1 to 0.5% by weight, particularly preferably from 0.25 to 0.35% by weight, based on the total weight of the catalyst, and at least 60% by weight, particularly preferably 80% by weight, of the active metal, based on the total amount of active metal, is present in the shell of the catalyst to a penetration depth of 200 μm. The data given above are determined by means of SEM (scanning electron microscopy) EPMA (electron probe microanalysis)-EDXS (energy dispersive X-ray spectroscopy) and represent mean values. Further information regarding the above-described measurement methods and techniques are disclosed, for example, in "Spectroscopy in Catalysis" by J. W. Niemantsverdriet, VCH, 1995.

In the coated catalyst, the predominant amount of the active metal is present in the shell to a penetration depth of 200 μm, i.e. near the surface of the coated catalyst. In contrast, no active metal or only a very small amount of active metal is present in the interior (core) of the catalyst. It has surprisingly been found that the catalyst variant III has, despite the small amount of active metal, a very high activity in the hydrogenation of organic compounds comprising hydrogenatable groups, in particular in the hydrogenation of carbocyclic aromatic groups, at very good selectivities. In particular, the activity of catalyst variant III does not decrease over a long hydrogenation time.

Very particular preference is given to a coated catalyst in which no active metal can be detected in the interior of the catalyst, i.e. active metal is present only in the outer shell, for example in a zone to a penetration depth of from 100 to 200 μm.

In a further particularly preferred embodiment, active metal particles can be detected only in the outermost 200 μm, preferably 100 μm, very particularly preferably 50 μm (penetration depth), of the coated catalyst by means of (FEG)-TEM (field emission gun-transmission electron microscopy) with EDXS. Particles smaller than 1 nm cannot be detected.

As active metal, it is possible to use either ruthenium alone or ruthenium together with at least one further metal of transition group IB, VIIB or VII of the Periodic Table of the Elements (CAS version). Further active metals which are suitable in addition to ruthenium are, for example, platinum, rhodium, palladium, iridium, cobalt or nickel or a mixture of two or more thereof. Among the metals of transition groups IB and/or VIIB of the Periodic Table of the Elements which can likewise be used, suitable metals are, for example, copper and/or rhenium. Preference is given to using ruthenium alone as active metal or together with platinum or iridium in the coated catalyst; very particular preference is given to using ruthenium alone as active metal.

The coated catalyst displays the abovementioned very high activity at a low loading with active metal of <1% by weight, based on the total weight of the catalyst. The amount of active metal in the coated catalyst according to the invention is preferably from 0.1 to 0.5% by weight, particularly preferably from 0.25 to 0.35% by weight. It has been found that the penetration depth of the active metal into the support material is dependent on the loading of the catalyst variant III with active metal. Even at a loading of the catalyst variant III with 1% by weight or more, e.g. at a loading with 1.5% by weight, a significant amount of active metal is present in the interior of the catalyst, i.e. at a penetration depth of from 300 to 1000 μm, and this impairs the activity of the hydrogenation catalyst, in particular the activity over a long hydrogenation time, particularly in the case of fast reactions, with a deficiency of hydrogen being able to occur in the interior of the catalyst (core).

In the coated catalyst, at least 60% by weight of the active metal, based on the total amount of active metal, is present in the shell of the catalyst to a penetration depth of 200 μm. Preference is given to at least 80% by weight of the active metal in the coated catalyst, based on the total amount of active metal, being present in the shell of the catalyst to a penetration depth of 200 μm. Very particular preference is given to a coated catalyst in which no active metal can be detected in the interior of the catalyst, i.e. active metal is present only in the outermost shell, for example in a zone to a penetration depth of from 100 to 200 μm. In a further preferred embodiment, 60% by weight, preferably 80% by weight, based on the total amount of active metal, is present in the shell of the catalyst to a penetration depth of 150 μm. The abovementioned data are determined by means of SEM (scanning electron microscopy) EPMA (electron probe microanalysis)-EDXS (energy dispersive X-ray spectroscopy) and are mean values. To determine the penetration depth of the active metal particles, a number of catalyst particles (e.g. 3, 4 or 5) are cut and ground perpendicular to the extrudate axis (when the catalyst is in the form of extrudates). The profiles of the active metal/Si concentration ratios are then determined by means of line scans. On each measurement line, a number, for example from 15 to 20, measurement points at equal intervals are measured; the size of the measurement spot is about 10 μm*10 μm. After integration of the amount of active metal over the depth, the frequency of the active metal in a zone can be determined.

Very particular preference is given to the amount of active metal, based on the concentration ratio of active metal to Si, on the surface of the coated catalyst determined by means of SEM EPMA-EDXS being from 2 to 25%, preferably from 4 to 10%, particularly preferably from 4 to 6%. The surface analysis is carried out by means of analyses of regions having dimensions of 800 μm×2000 μm at an information depth of about 2 μm. The elemental composition is determined in % by weight (normalized to 100%). The mean concentration ratio (active metal/Si) is determined over 10 measurement regions.

For the purposes of the present invention, the surface of the coated catalyst is the outer shell of the catalyst to a penetration depth of about 2 μm. This penetration depth corresponds to the information depth in the abovementioned surface analysis.

Very particular preference is given to a coated catalyst in which the amount of active metal, based on the weight ratio of active metal to Si (weight/weight in %), on the surface of the coated catalyst is from 4 to 6%, at a penetration depth of 50 μm is from 1.5 to 3% and in a penetration depth range from 50 to 150 μm is from 0.5 to 2%, determined by means of SEM EPMA (EDXS). The values specified are mean values.

Furthermore; the size of the active metal particles preferably decreases with increasing penetration depth, determined by means of (FEG)-TEM analysis.

The active metal is preferably present either partly or completely in crystalline form in the coated catalyst. In preferred cases, very finely crystalline active metal can be detected in the shell of the coated catalyst by means of SAD (selected area diffraction) or XRD (X-ray diffraction).

The coated catalyst can further comprise alkaline earth metal ions (($M^{2+}$), i.e. M=Be, Mg, Ca, Sr and/or Ba, in particular Mg and/or Ca, very particularly preferably Mg. The content of alkaline earth metal ion(s) ($M^{2+}$) in the catalyst is preferably from 0.01 to 1% by weight, in particular from 0.05 to 0.5% by weight, very particularly preferably from 0.1 to 0.25% by weight, in each case based on the weight of silicon dioxide support material.

An important constituent of catalyst variant III is the support material based on silicon dioxide, in general amorphous silicon dioxide. In this context, the term "amorphous" means that the proportion of crystalline silicon dioxide phases is less than 10% by weight of the support material. However, the support materials used for preparing the catalysts can have superstructures formed by a regular arrangement of pores in the support material.

As support materials, it is basically possible to use amorphous types of silicon dioxide which comprise at least 90% by weight of silicon dioxide, with the remaining 10% by weight, preferably not more than 5% by weight, of the support material also being able to be another oxidic material, e.g. MgO, CaO, $TiO_2$, $ZrO_2$, $Fe_2O_3$ and/or alkali metal oxide.

In a preferred embodiment of the invention, the support material is halogen-free, in particular chlorine-free, i.e. the halogen content of the support material is less than 500 ppm by weight, e.g. in the range from 0 to 400 ppm by weight. Preference is thus given to a coated catalyst which comprises less than 0.05% by weight of halide (determined by ion chromatography), based on the total weight of the catalyst.

Preference is given to support materials which have a specific surface area in the range from 30 to 700 $m^2/g$, preferably from 30 to 450 $m^2/g$ (BET surface area in accordance with DIN 66131).

Suitable amorphous support materials based on silicon dioxide are known to those skilled in the art and are commercially available (cf., for example, O. W. Flörke, "Silica" in Ullmann's Encyclopedia of Industrial Chemistry 6th Edition on CD-ROM). They can be of natural origin or can have been produced synthetically. Examples of suitable amorphous support materials based on silicon dioxide are silica gels, kieselguhr, pyrogenic silicas and precipitated silicas. In a preferred embodiment of the invention, the catalysts have silica gels as support materials.

Depending on the embodiment of the invention, the support material can have a different form. If the process in which the coated catalysts are used is a suspension process, the support material is usually used in the form of a fine powder for producing the catalysts. The powder preferably has particle sizes in the range from 1 to 200 μm, in particular from 1 to 100 μm. When the coated catalyst according to the invention is used in fixed beds of catalyst, it is usual to use shaped bodies composed of the support material which can be obtained, for example, by extrusion, ram extrusion or tableting and can, for example, have the shape of spheres, pellets, cylinders, extrudates, rings or hollow cylinders, stars and the like. The dimensions of these shaped bodies are usually in the range from 0.5 mm to 25 mm. Catalyst extrudates having extrudate diameters of from 1.0 to 5 mm and extrudate lengths of from 2 to 25 mm are frequently used. In general, higher activities can be achieved when using relatively small extrudates, but these often do not have sufficient mechanical stability in the hydrogenation process. Very particular preference is therefore given to using extrudates having extrudate diameters in the range from 1.5 to 3 mm.

Preferred Processes Using the Catalysts

The above-described catalysts (catalyst variants I, II and III and the subvariants mentioned) are preferably used as hydrogenation catalyst. They are suitable, in particular, for the hydrogenation of organic compounds comprising hydrogenatable groups. The hydrogenating groups can be groups which have the following structural units: C—C double bonds, C—C triple bonds, aromatic groups, C—N double bonds, C—N triple bonds, C—O double bonds, N—O double bonds, $NO_2$ groups, with the groups also being able to be comprised in polymers or cyclic structures, e.g. in unsaturated heterocycles. The hydrogenatable groups can in each case occur one or more times in the organic compounds. It is also possible for the organic compounds to have two or more different hydrogenatable groups from among those mentioned. In the latter case, it is possible, depending on the hydrogenation conditions, for one or more of the hydrogenatable groups to be hydrogenated. It is also possible for a functional group which remains intact to be present. This is the case, for instance, for —OH or NH functions which are present on an aromatic radical which is hydrogenated to the corresponding carbocyclic group with retention of the functional group described.

The above-described catalysts are preferably used for the hydrogenation of a carbocyclic aromatic group to the corresponding carbocyclic aliphatic group. Here, complete hydrogenation of the aromatic group particularly preferably occurs, with the expression complete hydrogenation referring to a conversion of the compound to be hydrogenated of generally >98%, preferably >99%, particularly preferably >99.5%, very particularly preferably >99.9%, in particular >99.99% and especially >99.995%.

When the above-described catalyst variants I, II and III are used for the hydrogenation of benzene to cyclohexane, the typical cyclohexane specifications which require a residual benzene content of >100 ppm (corresponding to a benzene conversion of >99.99%) are thus adhered to. The benzene conversion in a hydrogenation of benzene using the coated catalyst according to the invention is preferably >99.995%.

When the catalyst variants I, II and/or III are used for the hydrogenation of aromatic dicarboxylic esters, in particular phthalic esters to the corresponding dialkyl cyclohexanedicarboxylates, the typical specifications which require a residual content of the aromatic dicarboxylic ester, in particular residual phthalic ester content, of <100 ppm (corresponding to a conversion of >99.99%) are thus likewise adhered to. The conversion in a hydrogenation of aromatic dicarboxylic esters, in particular phthalic esters, using the coated catalyst according to the invention is preferably >99.995%.

The present patent application therefore further provides a process for the hydrogenation of an organic compound comprising hydrogenatable groups, preferably for the hydrogenation of a carbocyclic aromatic group to the corresponding carbocyclic aliphatic group, with any functional groups present, for example —OH or NH groups remaining intact in the hydrogenation, which process has a regeneration step in addition to the hydrogenation step.

The carbocyclic aromatic group is preferably part of an aromatic hydrocarbon which has the following general formula:

$$(A)\text{-}(B)_n$$

where the symbols have the following meanings:

A is, independently, aryl or heteroaryl and is preferably selected from among phenyl, diphenyl, benzyl, dibenzyl, naphthyl, anthracene, pyridyl and quinoline, particularly preferably phenyl or naphthyl, n is from 0 to 5, preferably from 0 to 4, particularly preferably from 0 to 3, in particular when A is a 6-membered aryl or heteroaryl ring; when A is a 5-membered aryl or heteroaryl ring, n is preferably from 0 to 4; regardless of the ring size, n is particularly preferably from 0 to 3, very particularly preferably from 0 to 2 and in particular from 0 to 1; the other carbon atoms or heteroatoms of A which do not bear any substituents B bear hydrogen atoms or if appropriate no substituent;

the radicals B are selected independently from the group consisting of alkyl, alkenyl, alkynyl, substituted alkyl, substituted alkenyl, substituted alkynyl, heteroaryl, substituted heteroalkyl, heteroalkenyl, substituted heteroalkenyl, heteroalkynyl, substituted heteroalkynyl, cycloalkyl, cycloalkenyl, substituted cycloalkyl, substituted cycloalkenyl, COOR, where R is H, alkyl, substituted alkyl, cycloalkyl, substituted cycloalkyl, aryl or substituted aryl, halogen, hydroxy, alkoxy, aryloxy, carbonyl, amino, amido and phosphino; the radicals B are preferably selected independently from among $C_{1-6}$-alkyl, $C_{1-6}$-alkenyl, $C_{1-6}$-alkynyl, $C_{3-8}$-cycloalkyl, $C_{3-8}$-cycloalkenyl, COOR, where R is H or $C_{1-12}$-alkyl, hydroxy, alkoxy, aryloxy, amino and amido; particular preference is given to the radicals B each being, independently of one another, $C_{1-6}$-alkyl, COOR, where R is H or $C_{1-12}$-alkyl, amino, hydroxy or alkoxy.

The expression "independently (of one another)" means that when n is 2 or more, the substituents B can be identical or different radicals from the groups mentioned.

For the purposes of the present patent application, the term alkyl refers to branched or linear, saturated acyclic hydrocarbon radicals, for example alkyl radicals having from 1 to 50 carbon atoms, preferably from 1 to 20 carbon atoms.

In the abovementioned group COOR, R is H or branched or linear alkyl, preferably H or $C_{1-12}$-alkyl. Preferred alkyl groups are $C_{4-10}$-alkyl groups, particularly preferably $C_{8-10}$-alkyl groups. These can be branched or unbranched and are preferably branched. Alkyl groups having more than three carbon atoms can be isomer mixtures of various alkyl groups having the same number of carbon atoms. An example is a $C_9$-alkyl group, which can be an isononyl group, i.e. an isomer mixture of various $C_9$-alkyl groups. The same applies to, for example, a $C_8$-alkyl group. Such isomer mixtures are obtained from the alcohols corresponding to the alkyl groups which, owing to their method of production which is known to those skilled in the art, are obtained as isomer mixtures.

For the purposes of the present application, the term alkenyl refers to branched or unbranched acyclic hydrocarbon radicals which have at least one carbon-carbon double bond. Suitable alkenyl radicals are, for example, 2-propenyl, vinyl, etc. The alkenyl radicals preferably have from 2 to 50 carbon atoms, particularly preferably from 2 to 20 carbon atoms, very particularly preferably from 2 to 6 carbon atoms and in particular 2 or 3 carbon atoms. Furthermore, the term alkenyl encompasses radicals which have either a cis orientation or a trans orientation.

For the purposes of the present patent application, the term alkynyl refers to branched or unbranched acyclic hydrocarbon radicals which have at least one carbon-carbon triple bond. The alkynyl radicals preferably have from 2 to 50 carbon atoms, particularly preferably from 2 to 20 carbon atoms, very particularly preferably from 1 to 6 carbon atoms and in particular 2 or 3 carbon atoms.

The terms substituted alkyl, substituted alkenyl and substituted alkynyl refer to alkyl, alkenyl and alkynyl radicals in which one or more hydrogen atoms bound to a carbon atom of these radicals have been replaced by another group. Examples of such other groups are heteroatoms, halogen, aryl, substituted aryl, cycloalkyl, cycloalkenyl, substituted cycloalkyl, substituted cycloalkenyl and combinations thereof. Examples of suitable substituted alkyl radicals are benzyl, trifluoromethyl etc.

The terms heteroalkyl, heteroalkenyl and heteroalkynyl refer to alkyl, alkenyl and alkynyl radicals in which one or more of the carbon atoms in the carbon chain have been replaced by a heteroatom selected from among N and O. The bond between the heteroatom and a further carbon atom can be saturated or, if appropriate, unsaturated.

For the purposes of the present patent application, the term cycloalkyl refers to saturated cyclic nonaromatic hydrocarbon radicals which are made up of a single ring or a plurality of fused rings. Suitable cycloalkyl radicals are, for example, cyclopentyl, cyclohexyl, cyclooctanyl, bicyclooctyl, etc. The cycloalkyl radicals preferably have from 3 to 50 carbon atoms, particularly preferably from 3 to 20 carbon atoms, very particularly preferably from 3 to 8 carbon atoms and in particular from 3 to 6 carbon atoms.

For the purposes of the present patent application, the term cycloalkenyl refers to partly unsaturated, cyclic nonaromatic hydrocarbon radicals which have a single ring or a plurality of fused rings. Suitable cycloalkenyl radicals are, for example, cyclopentenyl, cyclohexenyl, cyclooctenyl etc. The cycloalkenyl radicals preferably have from 3 to 50 carbon atoms, particularly preferably from 3 to 20 carbon atoms, very particularly preferably from 3 to 8 carbon atoms and in particular from 3 to 6 carbon atoms.

Substituted cycloalkyl and substituted cycloalkenyl radicals are cycloalkyl and cycloalkenyl radicals in which one or more hydrogen atoms of any particular carbon atom of the carbon ring are replaced by another group. Such other groups are, for example, halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, an aliphatic heterocyclic radical, a substituted aliphatic heterocyclic radical, heteroaryl, substituted heteroaryl, alkoxy, aryloxy, boryl, phosphino, amino, silyl and combinations thereof.

Examples of substituted cycloalkyl and cycloalkenyl radicals are 4-dimethylaminocyclohexyl, 4,5-dibromocyclohept-4-enyl.

For the purposes of the present patent application, the term aryl refers to aromatic radicals which have a single aromatic ring or a plurality of aromatic rings which are fused, linked via a covalent bond or linked by means of a suitable unit, e.g. a methylene or ethylene unit. Such suitable units can also be carbonyl units as in benzophenol or oxygen units as in diphenyl ether or nitrogen units as in diphenylamine. The aromatic ring or aromatic rings is/are, for example, phenyl, naphthyl, biphenyl, diphenyl ether, diphenylamine or benzophenone. The aryl radicals preferably have from 6 to 50 carbon atoms, particularly preferably from 6 to 20 carbon atoms, very particularly preferably from 6 to 8 carbon atoms.

Substituted aryl radicals are aryl radicals in which one or more hydrogen atoms bound to carbon atoms of thelaryl radical have been replaced by one or more other groups. Suitable other groups are alkyl, alkenyl, alkynyl, substituted alkyl, substituted alkenyl, substituted alkynyl, cycloalkyl, cycloalkenyl, substituted cycloalkyl, substituted cycloalkenyl, heterocyclo, substituted heterocyclo, halogen, halogen-substituted alkyl (e.g. $CF_3$), hydroxy, amino, phosphino, alkoxy and both saturated and unsaturated cyclic hydrocarbons which may be fused onto the aromatic ring or rings or be linked thereto via a bond or be linked to one another via a suitable group. Suitable groups have been mentioned above.

Heteroaryl radicals are aryl radicals in which one or more of the carbon atoms of the aromatic ring of the aryl radical has/have been replaced by a heteroatom selected from among N and O.

Substituted heteroaryl radicals are substituted aryl radicals in which one or more of the carbon atoms of the aromatic ring of the substituted aryl radical has/have been replaced by a heteroatom selected from among N and O.

For the purposes of the present patent application, the term heterocyclo refers to a saturated, partly unsaturated or unsaturated cyclic radical in which one or more carbon atoms of the radical have been replaced by a heteroatom, e.g. N or O (the term "heterocyclo" also encompasses the abovementioned heteroaryl radicals). Examples of heterocyclo radicals are piperazinyl, morpholinyl, tetrahydropyranyl, tetrahydrofuranyl, piperidinyl, pyrolidinyl, oxazolinyl, pyridyl, pyrazyl, pyridazyl, pyrimidyl.

Substituted heterocyclo radicals are heterocyclo radicals in which one or more hydrogen atoms bound to one of the ring atoms have been replaced by another group. Suitable other groups are halogen, alkyl, substituted alkyl, aryl, substituted aryl, heteroaryl, substituted heteroaryl, alkoxy, aryloxy, boryl, phosphino, amino, silyl and combinations thereof.

Alkoxy radicals are radicals of the general formula —$OZ^1$, where $Z^1$ is selected from among alkyl, substituted alkyl, cycloalkyl, substituted cycloalkyl, heterocycloalkyl, substituted heterocycloalkyl, silyl and combinations thereof. Suitable alkoxy radicals are, for example, methoxy, ethoxy, benzyloxy, t-butoxy, etc. The term aryloxy refers to radicals of the general formula —$OZ^1$ in which $Z^1$ is selected from among aryl, substituted aryl, heteroaryl, substituted heteroaryl and combinations thereof. Suitable aryloxy radicals are phenoxy, substituted phenoxy, 2-pyridinoxy, 8-quinolinoxy, etc.

In a preferred embodiment, A is phenyl, n is from 0 to 3 and B is $C_{1-6}$-alkyl, COOR, where R is H or $C_{1-12}$-alkyl, amino, hydroxy or alkoxy. The hydrogenation process of the invention is preferably carried out so that the phenyl group is completely hydrogenated to the corresponding cyclohexyl group.

Preferred compounds which can be hydrogenated to their corresponding cyclohexyl derivatives are mentioned below.

In a preferred embodiment of the hydrogenation process, the aromatic hydrocarbon is selected from the group consisting of benzene and alkyl-substituted benzenes such as toluene, ethylbenzene, xylene (o-, m-, p- or isomer mixture) and mesitylene (1,2,4 or 1,3,5 or isomer mixture). Thus, preference is given to hydrogenating benzene to cyclohexane and the alkyl-substituted benzenes such as toluene, ethylbenzene, xylene and mesitylene to alkyl-substituted cyclohexanes such as methylcyclohexane, ethylcyclohexane, dimethylcyclohexane and trimethylcyclohexane in the process of the invention. It is also possible to hydrogenate any mixtures of the abovementioned aromatic hydrocarbons to mixtures of the corresponding cyclohexanes. For example, any mixtures comprising two or three compounds selected from among benzene, toluene and xylene can be hydrogenated to mixtures comprising two or three compounds selected from cyclohexane, methylcyclohexane and dimethylcyclohexane.

In a further preferred embodiment of the invention, the aromatic hydrocarbon is selected from among cumene, diphenylmethane, tribenzenes, tetrabenzenes, pentabenzenes and hexabenzenes, triphenylmethane, alkyl-substituted naphthalenes, naphthalene, alkyl-substituted anthracenes, anthracene, alkyl-substituted tetralins, tetralin and diisononyl phthalate. A preferred example is the hydrogenation of naphthalene to tetralin or decalin.

In a further preferred embodiment of the hydrogenation process, the aromatic hydrocarbon is selected from the group consisting of phenol, alkyl-substituted phenols such as 4-tert-butylphenol and 4-nonylphenol, bis(p-hydroxyphenyl)methane and bis(p-hydroxyphenyl)dimethylmethane. Preference is thus given to hydrogenating phenol to cyclohexanol, the alkyl-substituted phenols such as 4-tert-butylphenol and 4-nonylphenol to alkyl-substituted cyclohexanols such as 4-tert-butylcyclohexanol and 4-nonylcyclohexanol, bis(p-hydroxyphenyl)methane to bis(p-hydroxycyclohexyl)methane and bis(p-hydroxyphenyl)dimethylmethane to bis(p-hydroxycyclohexyl)dimethylmethane in the process of the invention. In one variant of this preferred embodiment, the hydroxy function of the phenol is etherified, preferably to form alkoxyphenols. Preference is given to using an ethoxyphenol which may be unsubstituted or bear substituents.

In a further preferred embodiment of the hydrogenation process of the invention, the aromatic hydrocarbon is selected from the group consisting of aniline, alkyl-substituted aniline, N,N-dialkylaniline, diaminobenzene, bis(p-aminophenyl)methane and bis(p-aminotolyl)methane. Preference is thus given to hydrogenating aniline to cyclohexylamine, alkyl-substituted aniline to alkyl-substituted cyclohexylamine, N,N-dialkylaniline to N,N-dialkylcyclohexylamine, 2,6-dimethylaniline to 2,6-dicyclohexylamine, diaminobenzene to diaminocyclohexane, bis(p-aminophenyl)methane to bis(p-aminocyclohexyl)methane, (2-aminophenyl)-(4-aminophenyl)methane to (2-aminocyclohexyl)-(4-aminocyclohexyl)methane and bis(p-aminotolyl)methane to bis(p-aminomethylcyclohexyl)methane in the process of the invention.

In a further preferred embodiment of the hydrogenation process of the invention, the aromatic hydrocarbon is selected from the group consisting of aromatic carboxylic acids such as phthalic acid and aromatic carboxylic esters such as $C_{1-12}$-alkyl esters of phthalic acid, with the $C_{1-12}$-alkyl radicals being able to be linear or branched, e.g. dimethyl phthalate, di-2-propylheptyl phthalate, di-2-ethylhexyl phthalate, dioctyl phthalate, diisononyl phthalate. Preference is thus given to hydrogenating aromatic carboxylic acids such as phthalic acid to cycloaliphatic carboxylic acids such as tetrahydrophthalic acid and aromatic carboxylic esters such as $C_{1-12}$-alkyl esters of phthalic acid to aliphatic carboxylic esters such as $C_{1-12}$-alkyl esters of tetrahydrophthalic acid, e.g. dimethyl phthalate to dimethylcyclohexanedicarboxylate, di-2-propylheptyl phthalate to di-2-propylheptyl cyclohexanedicarboxylate, di-2-ethylhexyl phthalate to di-2-ethylhexyl cyclohexanedicarboxylate, dioctyl phthalate to dioctyl cyclohexanedicarboxylate and diisononyl phthalate to diisononyl cyclohexanedicarboxylate in the process of the invention.

In a further embodiment which may be possible, the present patent application provides a process for the hydrogenation of aldehydes to the corresponding alcohols. Preferred aldehydes are monosaccharides and disaccharides such as glucose, lactose and xylose. The monosaccharides and disaccharides are hydrogenated to the corresponding sugar alcohols, e.g. glucose is hydrogenated to sorbitol, lactose is hydrogenated to lactitol and xylose is hydrogenated to xylitol.

Suitable monosaccharides and disaccharides and suitable hydrogenation conditions are disclosed, for example, in DE-A 101 28 205, with the coated catalyst according to the present invention being used in place of the catalyst disclosed in DE-A 101 28 205.

The hydrogenation process can be carried out in the liquid phase or in the gas phase. The hydrogenation process of the invention is preferably carried out in the liquid phase.

The hydrogenation process can be carried out in the absence of a solvent or diluent or in the presence of a solvent or diluent, i.e. it is not necessary to carry out the hydrogenation in solution.

As solvent or diluent, it is possible to use any suitable solvent or diluent. Possible solvents or diluents are in principle those which are able to dissolve the organic compound to be hydrogenated, preferably completely, or mix completely with this and are inert under the hydrogenation conditions, i.e. are not hydrogenated.

Examples of suitable solvents are cyclic and acyclic ethers, e.g. tetrahydrofuran, dioxane, methyl tert-butyl ether, dimethoxyethane, dimethoxypropane, dimethyldiethylene glycol, aliphatic alcohols such as methanol, ethanol, n-propanol or isopropanol, n-butanol, 2-butanol, isobutanol or tert-butanol, carboxylic esters such as methyl acetate, ethyl acetate, propyl acetate or butyl acetate, and also aliphatic ether alcohols such as methoxypropanol and cycloaliphatic compounds such as cyclohexane, methylcyclohexane and dimethylcyclohexane.

The amount of solvent or diluent used is not subject to any particular restrictions and can be selected freely according to requirements, but preference is given to amounts which lead to a from 3 to 70% strength by weight solution of the organic compound intended for hydrogenation. The use of a diluent is advantageous in order to avoid excessive evolution of heat in the hydrogenation process. Excessive evolution of heat can lead to deactivation of the catalyst and is therefore undesirable. Careful temperature control is therefore advantageous in the hydrogenation process of the invention. Suitable hydrogenation temperatures are mentioned below.

When a solvent is used, particular preference is given to using, for the purposes of the invention, the product formed in the hydrogenation, i.e. preferably the respective cycloaliphatic(s), as solvent, if appropriate together with other solvents or diluents. In any case, part of the product formed in the process can be mixed into the aromatics still to be hydrogenated. In the hydrogenation of benzene, cyclohexane is thus used as solvent in a particularly preferred embodiment. In the hydrogenation of phthalates, the corresponding dialkyl cyclohexanedicarboxylates are preferably used as solvents.

Based on the weight of the organic compound intended for hydrogenation, preference is given to mixing in from 1 to 30 times, particularly preferably from 5 to 20 times, in particular from 5 to 10 times, the amount of the product to be formed as solvent or diluent. In particular, the present invention provides a hydrogenation of the type under discussion here in which benzene is hydrogenated in the presence of the catalyst according to the invention to give cyclohexane.

The actual hydrogenation is usually carried out by a method analogous to the known hydrogenation processes for the hydrogenation of organic compounds having hydrogenatable groups, preferably for the hydrogenation of a carbocylic aromatic group to the corresponding carbocyclic aliphatic group, as are described in the prior art cited at the outset. For this purpose, the organic compound is, as a liquid phase or gaseous phase, preferably as a liquid phase, brought into contact with the catalyst in the presence of hydrogen. The liquid phase can be passed over a catalyst suspension (suspension process) or a fixed bed of catalyst (fixed-bed process).

The hydrogenation can be carried out either continuously or batchwise, with a continuous process being preferred. The process of the invention is preferably carried out in trickle reactors or in the flooded mode of operation according to the fixed-bed mode of operation. The hydrogen can be passed over the catalyst either in cocurrent with the solution of the starting material to be hydrogenated or in countercurrent.

Suitable apparatuses for carrying out a hydrogenation over a moving bed or fixed bed of catalyst are known from the prior art, e.g. from Ullmanns Enzyklopädie der Technischen Chemie, 4th edition, volume 13, p. 135 ff., and from P. N. Rylander, "Hydrogenation and Dehydrogenation" in Ullmann's Encyclopedia of Industrial Chemistry, 5th ed. on CD-ROM.

The hydrogenation can be carried out either under hydrogen at atmospheric pressure or under an increased hydrogen pressure, e.g. at an absolute hydrogen pressure of at least 1.1 bar, preferably at least 2 bar. In general, the absolute hydrogen pressure will not exceed a value of 325 bar and preferably 300 bar. The absolute hydrogen pressure is preferably in the range from 1.1 to 300 bar. The hydrogenation of benzene is carried out at, for example, a hydrogen pressure of generally=50 bar, preferably from 10 bar to 45 bar, particularly preferably from 15 to 40 bar, most preferably from 18 to 38 bar.

In the process, the reaction temperatures are generally at least 30° C. and will frequently not exceed a value of 250° C. The hydrogenation process is preferably carried out at temperatures in the range from 50 to 200° C., particularly preferably from 70 to 180° C., and very particularly preferably in the range from 80 to 160° C. The hydrogenation of benzene is carried out at, for example, temperatures in the range of generally from 75° C. to 170° C., preferably from 80° C. to 160° C.

Possible reaction gases include not only hydrogen but also hydrogen-comprising gases which comprise no catalyst poisons such as carbon monoxide or sulfur-comprising gases such as $H_2S$ or COS, e.g. mixtures of hydrogen with inert gases such as nitrogen or offgases from a reformer which usually further comprise volatile hydrocarbons. Preference is given to using pure hydrogen (purity≥99.9% by volume particularly ≥99.95% by volume, in particular ≥99.99% by volume).

Owing to the high catalyst activity, comparatively small amounts of catalyst based on the starting material used are required. Thus, in a batch suspension process, preference is given to using less than 5 mol %, e.g. from 0.2 mol % to 2 mol %, of active metal, based on 1 mol of starting material. In the case of a continuous hydrogenation process, the starting material to be hydrogenated is usually passed over the catalyst at a space velocity of from 0.05 to 3 kg/(l(catalyst)•h), in particular from 0.15 to 2 kg/(l(catalyst)•h).

Particularly Preferred Hydrogenation Processes

The hydrogenation of aromatics comprising a regeneration is generally carried out at a temperature of from 75° C. to 170° C., preferably from 80° C. to 160° C. The pressure is generally ≤50 bar, preferably from 10 to 45 bar, particularly preferably from 15 to 40 bar, very particularly preferably from 18 to 38 bar.

For example, benzene is hydrogenated to cyclohexane at a pressure of about 20 bar in the present process. Phthalates are hydrogenated to the corresponding cyclohexanedicarboxylic acid derivatives at a pressure of ≥10 bar. In particular, diisononyl phthalate is hydrogenated to diisononyl cyclohexanedicarboxylate at a pressure in the range from about 200 to about 250 bar.

The hydrogenation can generally be carried out in the suspension or fixed-bed mode, with the fixed-bed mode being preferred. The hydrogenation process is particularly preferably carried out with recirculation of liquid, with the heat of hydrogenation being able to be removed by means of a heat exchanger and utilized. The feed/recycle ratio when the hydrogenation process is carried out with recirculation of liquid is generally from 1:5 to 1:40, preferably from 1:10 to 1:30.

To achieve complete conversion, an after-reaction of the hydrogenation product mixture can be carried out. For this purpose, the hydrogenation product mixture can, subsequent to the hydrogenation process, be passed in the gas phase or in the liquid phase in a single pass through a downstream reactor. In the case of a liquid-phase hydrogenation, the reactor can be operated in the downflow mode or in a flooded state. The reactor is charged with the catalyst according to the invention or with another catalyst known to those skilled in the art.

Regeneration Step

In hydrogenation processes in which the catalysts described above are used, deactivation is observed after a period of operation of the catalyst. Such a deactivated ruthenium catalyst can be brought back to the state of the original activity by flushing. The activity can be restored to >90%, preferably >95%, more preferably >98%, in particular >99%, most preferably >99.5%, of the original value. The deactivation is attributed to traces or residues of water adsorbed on the catalyst. This can surprisingly be reversed by flushing with inert gas. The regeneration method of the invention can thus also be referred to as drying of the catalyst or removal of water from this.

"Flushing" means that the catalyst is brought into contact with inert gas. Normally, the inert gas is then for this purpose passed over the catalyst by means of suitable constructional measures known to those skilled in the art.

The flushing with inert gas is carried out at a temperature of from about 10 to 350° C., preferably from about 50 to 250° C., particularly preferably from about 70 to 180° C., most preferably from about 80 to 130° C.

The pressures applied during flushing are from 0.5 to 5 bar, preferably from 0.8 to 2 bar, in particular from 0.9 to 1.5 bar.

According to the invention, the treatment of the catalyst is preferably carried out using an inert gas. Preferred inert gases comprise nitrogen, carbon dioxide, helium, argon, neon, krypton, radon, xenon and mixtures thereof. Nitrogen is most preferred.

In a particular embodiment of the invention, the inventive method of regeneration is carried out without removal of the catalyst in the same reactor in which the hydrogenation has taken place. The flushing of the catalyst according to the present invention is particularly advantageously carried out at temperatures and pressures in the reactor which correspond to or are similar to those in the hydrogenation reaction, resulting in only a very brief interruption of the reaction process.

According to the present invention, the flushing with inert gas is carried out at a volume flow of from 20 to 200 standard l/h, preferably at a volume flow of from 50 to 200 standard l/h per liter of catalyst.

The flushing with inert gas is preferably carried out for a time of from 10 to 50 hours, particularly preferably from 10 to 20 hours. For example, the calculated drying time of the catalyst bed of an industrial cyclohexane production plant having an assumed moisture content of 2 or 5% by weight is approximately 18 or 30 hours, respectively. The flushing according to the method of the invention can be carried out either in a downward direction (downflow mode) or in an upward direction (upflow mode).

The present invention further provides an integrated process for the hydrogenation of an aromatic hydrocarbon in the presence of a ruthenium catalyst having a catalyst regeneration step, which comprises the following steps:
 (a) provision of at least one aromatic hydrocarbon and a ruthenium catalyst;
 (b) hydrogenation of the aromatic compound by contact with hydrogen in the presence of the ruthenium catalyst until the catalyst has a reduced hydrogenation activity,
 (c) regeneration of the catalyst by flushing with inert gas,
 (d) if appropriate, repetition of the steps (a) to (c).

The hydrogen used according to the invention preferably comprises no damaging catalyst poisons such as CO. For example, reformer gases can be used. Preference is given to using pure hydrogen as hydrogenation gas.

The method of the invention is also suitable for drying catalysts which have absorbed water during various procedures such as maintenance or storage.

The invention accordingly provides a method of drying and/or reactivating and/or regenerating a catalyst comprising ruthenium on a support material, in which the catalyst is treated with an inert gas at temperatures of from 20 to 350° C. After this treatment, the catalyst has a higher catalytic activity than before.

The invention is illustrated by the following examples:

EXAMPLES

Example of the Production of the Ruthenium Catalyst

A mesoporous/macroporous aluminum oxide support in the form of 3-5 mm spheres having a total volume of 0.44 cm$^3$/g, with 0.09 cm$^3$/g (20% of the total pore volume) being formed by pores having a diameter in the range from 50 nm to 10000 nm and 0.35 cm³/g (80% of the total pore volume) being formed by pores having a diameter in the range from 2 nm to 50 nm, a mean pore diameter in the region of 11 nm and a surface area of 286 m²/g was impregnated with an aqueous ruthenium (III) nitrate solution. The volume of solution taken during impregnation corresponded approximately to the pore volume of the support used. The support impregnated with the ruthenium (III) nitrate solution was subsequently dried at 120° C. and activated (reduced) in a stream of hydrogen at 200° C. The catalyst produced in this way comprised 0.5% by weight of ruthenium, based on the weight of the catalyst. The ruthenium surface area was 0.72 m²/g, and the ratio of ruthenium surface area to support surface area was 0.0027.

Example 1

Sorption Studies

The affinity of the catalyst for water was determined by means of measurements of the sorption of water vapor on the catalyst produced as described above (0.5% Ru/γ-Al₂O₃).

It was found that the catalyst sorbs an amount of water of 5% even at relatively low vapor pressures of 30%. If only traces of water are present in the reactor or in the starting materials, this water can be sorbed on the catalyst.

Example 2

Operating Life Experiment in the Hydrogenation of Benzene

In a plant for the preparation of cyclohexane using a ruthenium/aluminum oxide catalyst comprising 0.5% of Ru on a γ-Al₂O₃ support, a steady decrease in the catalyst activity and an increasing benzene content in the product stream are observed. Further monitoring of the reaction during a catalyst operating life test shows that the residual benzene content downstream of the main reactor in the hydrogenation of benzene increases from a few hundred ppm to some thousands of ppm over a period of operation of about 3400 hours. A calculation indicates that introduction of 16 620 kg/h of benzene having a water content of from 30 to 50 ppm introduces 0.8 kg of water per hour into the plant. In addition to this, there are a further 3.5 kg/h of water originating from the hydrogen gas.

When the plant was shut down after 3394 hours of operation, the plant ran with a residual benzene content of 0.2% at a WHSV of 0.6 $g_{benzene}/ml_{cat} \cdot h$. During shutdown, the plant was flushed with pressurized nitrogen at a temperature of 70-100° C. and then depressurized. After start-up, the plant gave a residual benzene content of from 0.01% to 0.04% at a WHSV of 0.6 $g_{benzene}/ml_{cat} \cdot h$.

This observed effect of drying of the catalyst was verified again after 7288 hours of operation. At a WHSV of 0.9 $g_{benzene}/ml_{cat} \cdot h$, the residual benzene content at the end of the plant was 0.2% and even rose to 0.56%. After shutdown of the plant, the catalyst was dried by means of 100 standard l/h of nitrogen at 110° C. for a period of 34 hours. After start-up of the plant at a WHSV of 0.6 $g_{benzene}/ml_{cat} \cdot h$, the residual benzene content was from 0.03% to 0.07%, which can be attributed to a significant increase in the catalyst activity as a result of drying.

In both cases, drying of the catalyst led to a significantly higher catalyst activity which is close to or equal to the original catalyst activity.

Example 3

Examination of the Influence of Water on the Hydrogenation of Benzene

To simulate the influence of water on the hydrogenation of benzene using a ruthenium catalyst, a series of autoclave experiments before and after saturation of the catalyst with water and after drying of the catalyst were carried out. A 5% strength solution of benzene in cyclohexane together with the ruthenium catalyst was placed in the pressure vessel, the mixture was heated to the reaction temperature of 100° C. and the course of the reaction at a hydrogen pressure of 32 bar was followed by regular sampling. The samples were subsequently analyzed by gas chromatography.

23 hydrogenation experiments were carried out, and the catalyst was subsequently placed in water. 13 further hydrogenation experiments were then carried out. The catalyst displayed a significantly lower but virtually constant activity. After drying of the catalyst in a stream of nitrogen at 100° C. in a reaction tube, 5 further experiments were carried out; the catalyst displayed a hydrogenation activity similar to that before saturation with water.

The experiments demonstrate that the activity of the ruthenium/aluminum oxide catalyst used decreases significantly after contact with water, but the catalyst can be reactivated again by drying in a stream of nitrogen and the initial activity can be virtually fully restored.

The invention claimed is:

1. An integrated method for hydrogenating a substance comprising aromatic groups consisting of the following steps:
   a) Providing a substance comprising aromatic groups and a ruthenium catalyst, wherein the ruthenium catalyst is selected from among the following groups:
      i) A catalyst comprising, as active metal, either ruthenium alone or ruthenium together with at least one metal of transition group IB, VIIB or VIII of the Periodic Table of the Elements in an amount of from 0.01 to 30% by weight, based on the total weight of the catalyst, applied to a support, wherein from 10 to 50% of the pore volume of the support is formed by macropores having a pore diameter in the range from 50 nm to 10000 nm and from 50 to 90% of the pore volume of the support being formed by mesopores having a pore diameter in the range from 2 to 60 nm, with the sum of the pore volumes being 100%; and
      ii) A coated catalyst comprising, as active metal, either ruthenium alone or ruthenium together with at least one further metal of transition group IB, VIIB or VIII of the Periodic Table of the Elements applied to a support comprising silicon dioxide as support material, wherein the amount of active metal is <1% by weight, based on the total weight of the catalyst, and at least 60% by weight of the active metal is present in a shell of the catalyst to a penetration depth of 200 μm determined by means of SEM-EPMA (EDXS);
   b) Hydrogenating the substance by contact with hydrogen in the presence of the ruthenium catalyst until the catalyst has a reduced hydrogenation activity,
   c) Regenerating the catalyst consisting of flushing with inert gas until an activity of >90% of the original activity has been attained, and
   d) Optionally, repeating the steps a) to c),
   wherein the pressure applied during flushing is from 0.5 to 5 bar; and wherein regenerating the catalyst according to step c) is carried out without removing the catalyst from the same reactor in which the hydrogenation according to step b) takes place.

2. The method according to claim 1, wherein the flushing with inert gas is carried out at a temperature of from 10 to 350° C.

3. The method according to claim 2, wherein the inert gas is selected from among nitrogen, carbon dioxide, helium, argon, neon and mixtures thereof.

4. The method according to claim 2, wherein the flushing with inert gas is carried out at a volume flow of from 20 to 200 standard l/h per liter of catalyst.

5. The method according to claim 1, wherein the inert gas is selected from among nitrogen, carbon dioxide, helium, argon, neon and mixtures thereof.

6. The method according to claim 5, wherein the flushing with inert gas is carried out at a volume flow of from 20 to 200 standard l/h per liter of catalyst.

7. The method according to claim 1, wherein the flushing with inert gas is carried out at a volume flow of from 20 to 200 standard l/h per liter of catalyst.

8. The method according to claim 7, wherein the inert gas is selected from among nitrogen, carbon dioxide, helium, argon, neon and mixtures thereof.

9. The method according to claim 1, wherein flushing with inert gas is carried out for a time of from 10 to 50 hours.

10. The method according to claim 9, wherein the flushing with inert gas is carried out at a volume flow of from 20 to 200 standard l/h per liter of catalyst.

11. The method according to claim 1, wherein the catalyst is a catalyst comprising as active metal, either ruthenium alone or ruthenium together with at least metal of transition group IB, VIIB or VIII of the Periodic Table of the Elements in an amount of from 0.01 to 30% by weight, based on the total weight of the catalyst, applied to a support, wherein from 10 to 50% of the pore volume of the support is formed by micropores having a pore diameter in the range from 50 nm to 10 000 nm and from 50 to 90% of the pore volume of the support being formed by mesopores having a pore diameter in the range from 2 to 50 nm, with the sum of the pore volumes being 100%, and the at least one metal of transition group IB, VIIB or VIII of the Periodic Table of the Elements is platinum, copper, rhenium, cobalt, nickel or a mixture of two or more thereof.

12. The method according to claim 1, wherein the catalyst is a coated catalyst comprising, as active metal, either ruthenium alone or ruthenium together with at least one further metal of transition group IB, VIIIB or VIII of the Periodic Table of the Elements applied to a support comprising silicon dioxide as support material, wherein the amount of active metal is <1% by weight, based on the total weight of the catalyst, and at least 60% by weight of the active metal is present in the shell of the catalyst to a penetration depth of 200 µm, determined by means of SEM-EPMA (EDXS), and the at least one metal of transition group IB, VIIB or VIII of the Periodic Table of the Elements is platinum, copper, rhenium, cobalt, nickel or a mixture of two or more thereof.

13. The method according to claim 1, wherein the catalyst is catalyst comprising, as active metal, either ruthenium alone or ruthenium together with at least one metal of transition group IB, VIIB or VIII of the Periodic Table of the Elements in an amount of from 0.01 to 30% by weight, based on the total weight of the catalyst, applied to a support, wherein from 10 to 50% of the pore volume of the support is formed by macropores having a pore diameter in the range from 50 nm to 10 000 nm and from 50 to 90% of the pore volume of the support being formed by mesopores having a pore diameter in the range from 2 to 50 nm, with the sum of the pore volumes being 100%, and the support is activated carbon, silicon carbide, aluminum oxide, titanium oxide, zirconium oxide, magnesium oxide, zinc oxide or a mixture of two or more thereof.

14. The method according claim 1, wherein benzene is converted into cyclohexane or diisononyl phthalate is converted into diisononylcyclohexanecarboxylate.

* * * * *